(12) United States Patent
Chen et al.

(10) Patent No.: US 9,816,940 B2
(45) Date of Patent: Nov. 14, 2017

(54) WAFER INSPECTION WITH FOCUS VOLUMETRIC METHOD

(71) Applicant: KLA-Tencor Corporation, Milpitas, CA (US)

(72) Inventors: Grace H. Chen, Los Gatos, CA (US); Keith Buckley Wells, Santa Cruz, CA (US); Markus B. Huber, Oakland, CA (US); Se Baek Oh, Millbrae, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/001,158

(22) Filed: Jan. 19, 2016

(65) Prior Publication Data

US 2016/0209334 A1    Jul. 21, 2016

Related U.S. Application Data

(60) Provisional application No. 62/105,979, filed on Jan. 21, 2015.

(51) Int. Cl.
*G01N 21/00* (2006.01)
*G01N 21/88* (2006.01)
*G01N 21/95* (2006.01)

(52) U.S. Cl.
CPC ..... *G01N 21/8851* (2013.01); *G01N 21/9501* (2013.01); *G01N 2021/8887* (2013.01)

(58) Field of Classification Search
CPC ....... G01N 2021/8887; G01N 21/8851; G01N 21/9501
USPC ...................... 356/237.1–237.6, 239.1–239.8
See application file for complete search history.

(56) References Cited

U.S. PATENT DOCUMENTS

| 7,170,075 B2 | 1/2007 | Oberski et al. |
| 7,551,272 B2 | 6/2009 | Vodanovic |
| 7,659,973 B2 | 2/2010 | Furman et al. |
| 7,826,047 B2 | 11/2010 | Shibata et al. |
| 7,904,845 B2 | 3/2011 | Fouquet et al. |
| 8,073,240 B2 | 12/2011 | Fischer et al. |
| 8,605,275 B2 | 12/2013 | Chen et al. |
| 8,810,646 B2 | 8/2014 | Hess |
| 2006/0178855 A1 | 8/2006 | Judell |
| 2011/0276935 A1 | 11/2011 | Fouquet et al. |
| 2011/0320149 A1 | 12/2011 | Lee et al. |
| 2012/0316855 A1 | 12/2012 | Park et al. |

(Continued)

FOREIGN PATENT DOCUMENTS

| WO | 0073977 A1 | 12/2000 |
| WO | 2014164894 A1 | 10/2014 |

OTHER PUBLICATIONS

"International Application Serial No. PCT/US2016/014167, Search Report mailed Apr. 29, 2016", 3 pgs.

*Primary Examiner* — Tri T Ton
(74) *Attorney, Agent, or Firm* — Kwan & Olynick, LLP

(57) ABSTRACT

Disclosed are methods and apparatus for detecting defects in a semiconductor sample. An inspection tool is used to collect intensity data sets at a plurality of focus settings from each of a plurality of xy positions of the sample. A polynomial equation having a plurality of coefficients is extracted for each of the xy position's collected intensity data sets as a function of focus setting. Each of the coefficients' set of values for the plurality of xy positions is represented with a corresponding coefficient image plane. A target set of coefficient image planes and a reference set of coefficient image planes are then analyzed to detect defects on the sample.

25 Claims, 12 Drawing Sheets

(56) References Cited

U.S. PATENT DOCUMENTS

| | | |
|---|---|---|
| 2013/0194569 A1 | 8/2013 | Lee et al. |
| 2014/0009601 A1 | 1/2014 | Cho et al. |
| 2014/0141536 A1 | 5/2014 | Levinski et al. |
| 2014/0168418 A1 | 6/2014 | Hess |
| 2014/0219544 A1 | 8/2014 | Wu et al. |

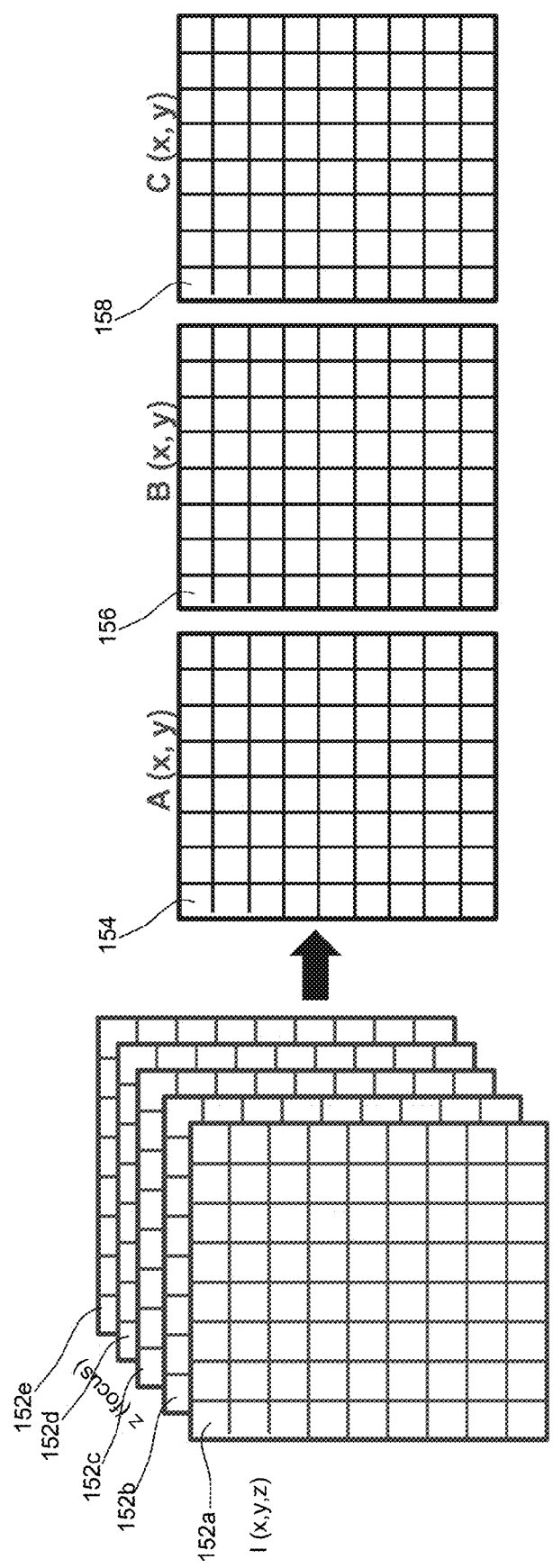

WAFER INSPECTION WITH FOCUS VOLUMETRIC METHOD

CROSS-REFERENCE TO RELATED APPLICATION

This application claims priority to U.S. Provisional Patent Application No. 62/105,979, entitled "Wafer Inspection With Focus Volumetric Method", filed 21 Jan. 2015 by Grace Chen, which application is incorporated herein by reference in its entirety for all purposes.

TECHNICAL FIELD OF THE INVENTION

The invention generally relates to the field of wafer and reticle inspection systems. More particularly the present invention relates to inspection techniques for increased sensitivity for defect detection.

BACKGROUND

Generally, the industry of semiconductor manufacturing involves highly complex techniques for fabricating integrating circuits using semiconductor materials that are layered and patterned onto a substrate, such as silicon. An integrated circuit is typically fabricated from a plurality of reticles. Generation of reticles and subsequent optical inspection of such reticles have become standard steps in the production of semiconductors. The fabrication of semiconductor devices, such as logic and memory devices, typically includes processing a semiconductor wafer using a large number of semiconductor fabrication processes with multiple reticles to form various features and multiple levels of the semiconductor devices. Multiple semiconductor devices may be fabricated in an arrangement on a single semiconductor wafer and then separated into individual semiconductor devices.

If there are defects on the reticle or wafer, the resulting semiconductor devices may not function properly. In a die-to-die inspection, images of a test die are compared to images of a reference die, and the differences are analyzed to detect defects. Conventionally, an optimal focus is found for a single target of the wafer, and then such optimal focus is used throughout the wafer. However, the optimal focus of the test and reference dies may vary for different wafer positions due to a number of factors so that different positions on the wafer are not inspected at an optimal focus setting. A die-to-die inspection may thereby collect images across the wafer that are not at optimal focus, which causes noise to be introduced into the inspection results so that defects are more difficult to detect.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method for detecting defects in a semiconductor sample is disclosed. An inspection tool is used to collect intensity data sets at a plurality of focus settings from each of a plurality of xy positions of the sample. A polynomial equation having a plurality of coefficients is extracted for each of the xy position's collected intensity data sets as a function of focus setting. Each of the coefficients' set of values for the plurality of xy positions is represented with a corresponding coefficient image plane. A target set of coefficient image planes and a reference set of coefficient image planes are then analyzed to detect defects on the sample.

In a specific implementation, intensity data is collected at the plurality of focus settings from a first set of one or more swaths before a next set of one or more swaths, and the number of the swaths in the first and next swaths, from which the intensity data is collected, is selected to be less than a thermal expansion time for affecting an actual focus position. In a further aspect, real-time xy and z encoder position data sets are collected from the inspection tool. Prior to extracting the polynomial equation for each of the xy positions' collected intensity data sets, the collected intensity data from each focus setting can be aligned based on the collected real-time xy position data. In a further aspect, intensity data is collected from each pair of swaths of xy positions at the plurality of focus settings before the aligning operation is performed for such intensity data.

In another embodiment, the method includes (i) initiating recording of xy encoder position data into an encoder buffer prior to collecting intensity data from a first one of the swaths at a first one of the focus settings, (ii) while the inspection tool's stage is turning around to setup for collecting intensity data from a second one of the swaths at the first focus setting, copying the xy encoder position data from the encoder buffer into a system memory for accessing for use in the aligning operation and then initiating recording of xy encoder position data into the encoder buffer prior to collecting intensity data from the second swath, (iii) while the inspection tool's stage is turning around to setup for collecting intensity data from the first swath at a second one of the focus settings after collecting intensity data from the second swath, copying the xy encoder position data from the encoder buffer into a system memory for accessing for use in the aligning operation and then initiating recording of xy encoder position data into the encoder buffer prior to collected intensity data from the first swath at the second focus setting, and (iv) repeating the operations of initiating recording and copying for subsequent pairs of swaths at each of the focus settings.

In another implementation, the analyzing operation is performed by (1) calculating a plurality of difference coefficient image planes having a plurality of difference coefficient values for each coefficient by subtracting each of the target set from each of the reference set and (2) analyzing the difference coefficient image planes to detect defects. In a further aspect, the difference coefficient image planes are analyzed by plotting an image point for the difference coefficient values at each xy position from the difference coefficient image planes into a scatter plot having an axis for each coefficient and clustering such scatter plot's image points into clusters of defects of interest image points, nuisance image points, or background image points. In yet a further aspect, the difference coefficient image planes are analyzed by projecting an image point for the difference coefficient values for each xy position from the difference coefficient image planes onto a unit sphere and clustering such projected image points into clusters of defects of interest image points, nuisance image points, or background image points.

In yet another example, the method includes (i) generating a plurality of difference images from intensity data sets collected from a target and a reference at each focus plane, (ii) combining the difference images to form a fused image across focus, and (iii) analyzing the fused image for defect detection. In a further aspect, the method includes (i) grouping the coefficients with similar values together so as to form a plurality of different segments, wherein each segment corresponds to different portion of an actual device structure, and (ii) analyzing the different segments with different stringency for detecting defects based on which type of actual devices correspond to the different segments.

In another implementation, the method includes analyzing a difference between intensity changes as a function of focus setting changes for each xy position in a second target set of intensity data sets and a second reference set of intensity data sets. In another aspect, the focus settings are comprised of pairs of focus setting, wherein each pair of focus setting is separated by a step value that is within a fraction of the depth of focus of the inspection system.

In an alternative embodiment, the invention pertains to an inspection system that includes an illumination optics module for generating and directing an incident beam towards a semiconductor sample at a plurality of focus settings and a collection optics module for collecting intensity data sets at a plurality of focus settings from each of a plurality of xy positions of the sample in response to the incident beam. The system further includes a controller that is configured to perform one or more of the above listed method operations.

These and other aspects of the invention are described further below with reference to the figures.

BRIEF DESCRIPTION OF THE DRAWINGS

FIG. 1B shows a diagrammatic representation of a process for extracting unique electromagnetic (EM) 3D volumetric (VM) parameters in accordance with certain embodiments of the present invention.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

The inspection techniques described herein may be implemented with respect to any suitable specimen having areas that are designed to be identical. One example specimen is a semiconductor reticle having multiple dies or cell arrays that are designed to be identical. Specimens can also take the form of a semiconductor reticle, a solar panel, a computer disk, etc.

An integrated circuit wafer typically includes multiple and identical device dies. Certain conventional semiconductor inspection modes are based on the comparison of features on the sample that are designed to be identical. Resulting anomalies from the comparison results may be identified as defect candidates. For instance, die-to-die inspection includes comparing two dies that are designed to be identical. Cell-to-cell inspection includes comparing two cells that are designed to be identical. Each difference detected between two images has the potential of being an actual defect, as compared to a "nuisance" defect or noise. That is, some of the detected defect candidates will have no effect on the corresponding portion of the integrated circuit and can, thus, be considered "false" defects.

A typical die-to-die inspection results may often be affected by the level of relative focus or defocus differences between the same die or cell areas that are being inspected and compared. For instance, two corresponding, but unequally focused die portions from two dies may result in detection of false defects or failure to detect real defects in such unequally focused die portions. Although there are many techniques for alleviating this focus problem in a die-to-die inspection, it is difficult to maintain an optimal focus across the entire wafer.

Figure 1A:
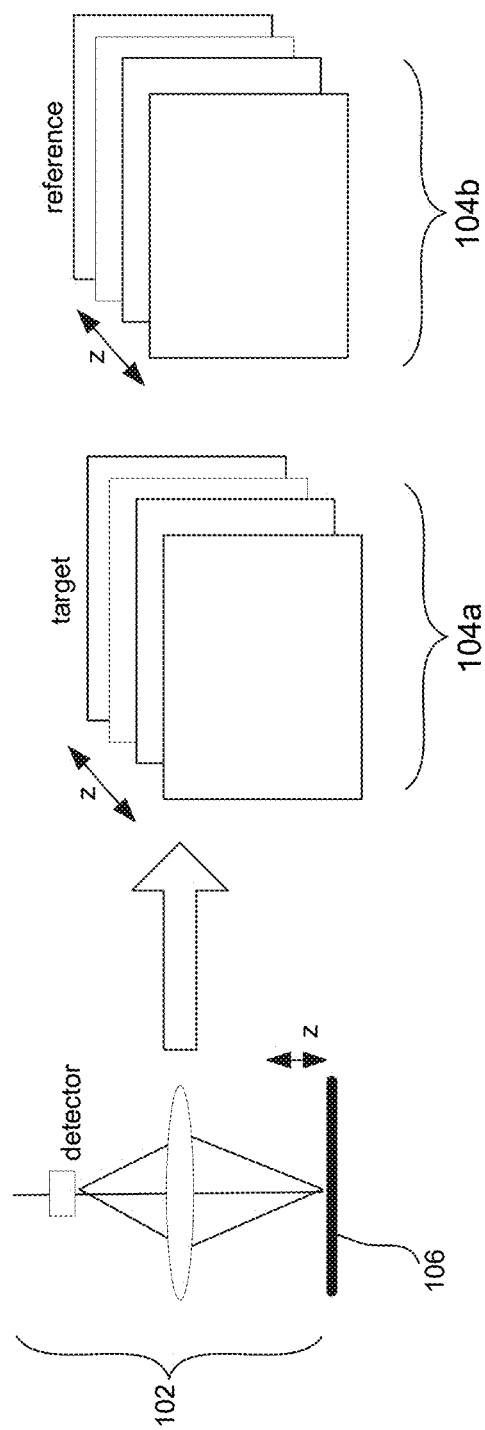
FIG. 1A is a diagrammatic representation of a volumetric inspection approach in accordance with one embodiment of the present invention.

Certain embodiments of the present invention include a die-to-die inspection in which images are obtained at a set of focus offset values across the entire wafer and used as a three dimensional (3D) focus data to enhance defect or nuisance differentiation for patterned wafer inspection. FIG. 1A is a diagrammatic representation of a volumetric inspection process in accordance with one embodiment of the present invention. In certain embodiments, an inspector 102 is used to obtain images of a sample 106, such as a semiconductor wafer, through a plurality of focus settings (z). A 3D focus data structure or a "volumetric" inspection data structure for each target (e.g., 104a) and reference (104b) is constructed by stacking the images acquired through different focus settings (z), which can then be used for various inspection applications.

In certain applications as further described below, the information from the 3D images are combined to (1) allow spatial segmentation, which achieves a finer resolution than what can be supported by standard optical resolution of conventional inspection systems, so as to support micro care area inspection applications, (2) enable extraction of electromagnetic (EM) volumetric parameters (VM parameters) to increase defect vs. background/nuisance separation, and (3) enable fusion of images that are constructed from such VM parameters so as to also increase defect vs. background/nuisance sensitivity. These applications, as well as other applications described below, can enhance the overall sensitivity, as well as other aspects, of wafer inspection.

Theoretically, acquiring wafer images at different focus heights can be expressed as adding known phase to the EM field that is returned from the wafer surface. It is known in the field of microscopy that phase interference can be effective to increase defect/background contrast. Performing defect detection by moving the sample at to different focus planes ultimately results in phase interference, which enables extraction of phase information from both background and defects. Detection sensitivity is enhanced using both phase and intensity data. Standard wafer inspection relies on intensity differences between a defect-of-interest (DOI) and background because intensity is directly detectable.

In a specific example, Fourier optics and focus phase perturbation effects can be combined so that the unique representation of focus phase interference with the EM wafer return can be expressed succinctly, for example, in a polynomial equation, such as described further below. FIG. 1B shows a diagrammatic representation of a process for extracting unique EM 3D volumetric parameters from 3D image data obtained from a sample in accordance with certain embodiments of the present invention. As shown, intensity (e.g., image) data sets (152a~152e) are collected from a sample at a plurality of x,y,z positions. Said in another way, each sample can be divided into a plurality of x,y positions, and each x,y position is imaged at multiple z focus settings. The 3D intensity data can be viewed as a plurality of intensity z planes so as to form a 3D image data structure. For instance, plane 152a represents the intensity data for a first focus setting and a plurality of xy positions, while plane 152b represents the intensity data for a second setting and the same xy positions as plane 152a. In fact, all the planes pertain to intensity data for the same set of xy positions.

The 3D image data may then be transformed into a plurality of polynomial equations for each xy position as a function of z. The polynomial for each xy position can have any suitable number of terms and corresponding coefficients. In the present example, a polynomial having three terms and corresponding coefficients A, B, and C is generated from the 3D image data. The number of terms that are extracted can vary. For instance, the number coefficients that are selected depends on the range of focus used to obtain volumetric data. About three coefficients (A~C) work well for a focus range close to 1 or 2 DOF (depth of focus), while about five coefficients (A~E) work well for a focus range close to 3 or 4 DOF. About seven coefficients (A~G) may be used for a focus range close to 5 or 6 DOF, and so on.

The focus step between each pair of consecutive through focus settings is generally controlled such that the images between the consecutive focus planes have enough correlation to enable good image alignment. The focus step of consecutive images can be selected to be within a fraction of the DOF of the system. Example focus setting steps are ⅓ or ½ of DOF.

The coefficient values for the different xy positions can each also be represented as an image plane or matrix of values. As shown, a first matrix 154 contains A coefficient values for each xy position; a second matrix 156 has B coefficient values for each xy position; and a third matrix 158 has C coefficient values for each xy position. The following Equation [1] may be generated for each set of intensity values for each xy position:

$$I(x,y,z)=A(x,y)\Delta z^2+B(x,y)\Delta z+C(x,y) \qquad \text{Equation [1]}$$

In summary, a VM formulism represents the behavior of I(z), the intensity of a particular wafer xy position and as a function of focus plane z, by an nth order polynomial. The polynomial coefficients [such as A(x, y), B(x, y), and C(x, y)] contain both intensity and phase information of the EM field generated from the wafer. In effect, electromagnetic (EM) volumetric parameters (VM parameters) are extracted from the 3D intensity data. These VM parameters can be used in numerous applications, as further described below, to enhance inspection.

Figure 2:
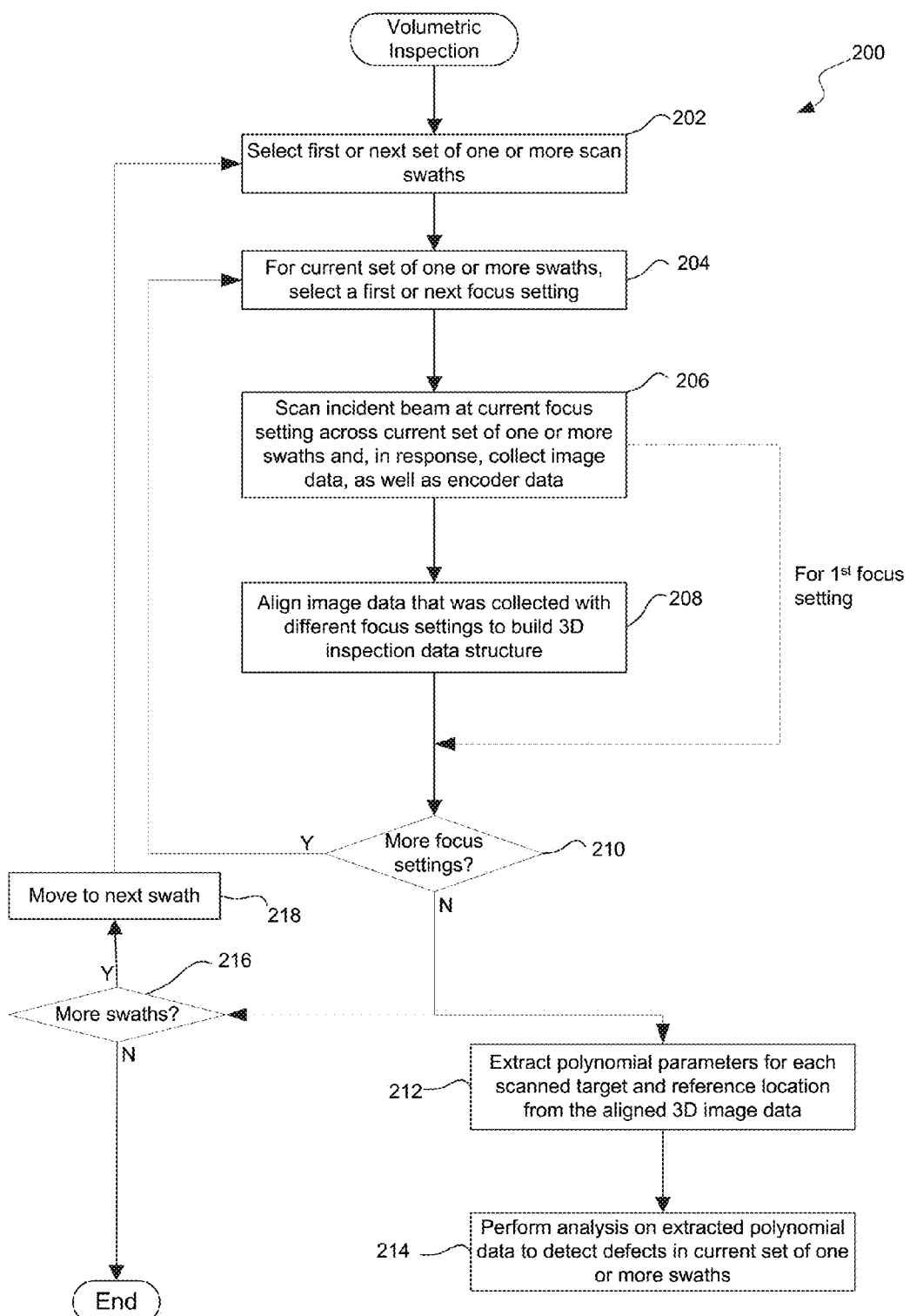
FIG. 2 is a flow chart illustrating a volumetric inspection process in accordance with one embodiment of the present invention.

FIG. 2 is a flow chart illustrating a volumetric inspection process 200 in accordance with one embodiment of the present invention. Initially, a first set of one or more scan swaths is selected in operation 202. A first focus setting is also selected for the current set of swaths in operation 204. An incident beam at the current focus setting is scanned across the current set of one or more swaths and, in response, image data is collected in operation 206. Encoder data may also be collected in operation 206.

Figure 3A:
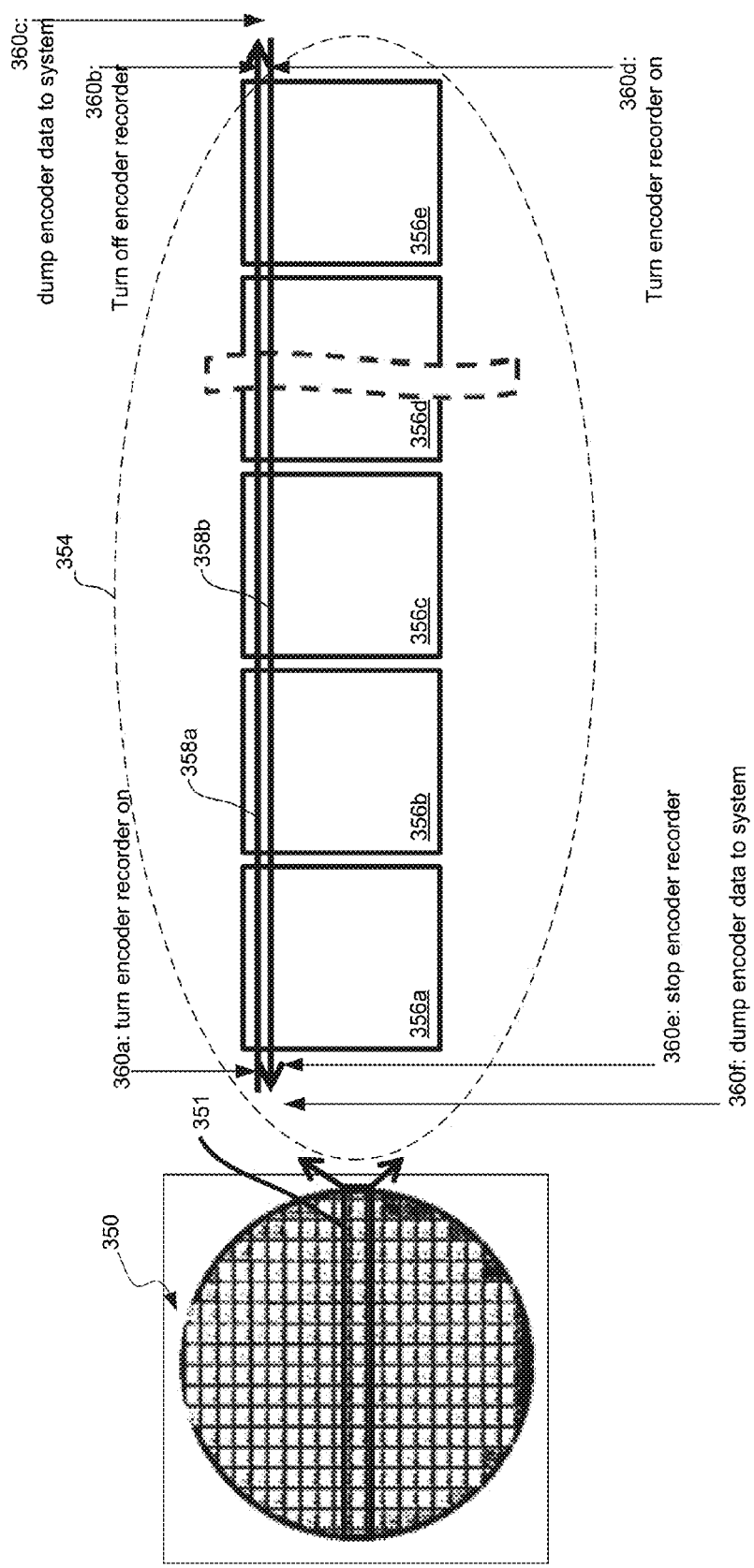
FIG. 3A is a diagrammatic representation of a wafer scanning process for facilitating construction of a 3D intensity data structure in accordance with a specific implementation of the present invention.
Figure 3B:
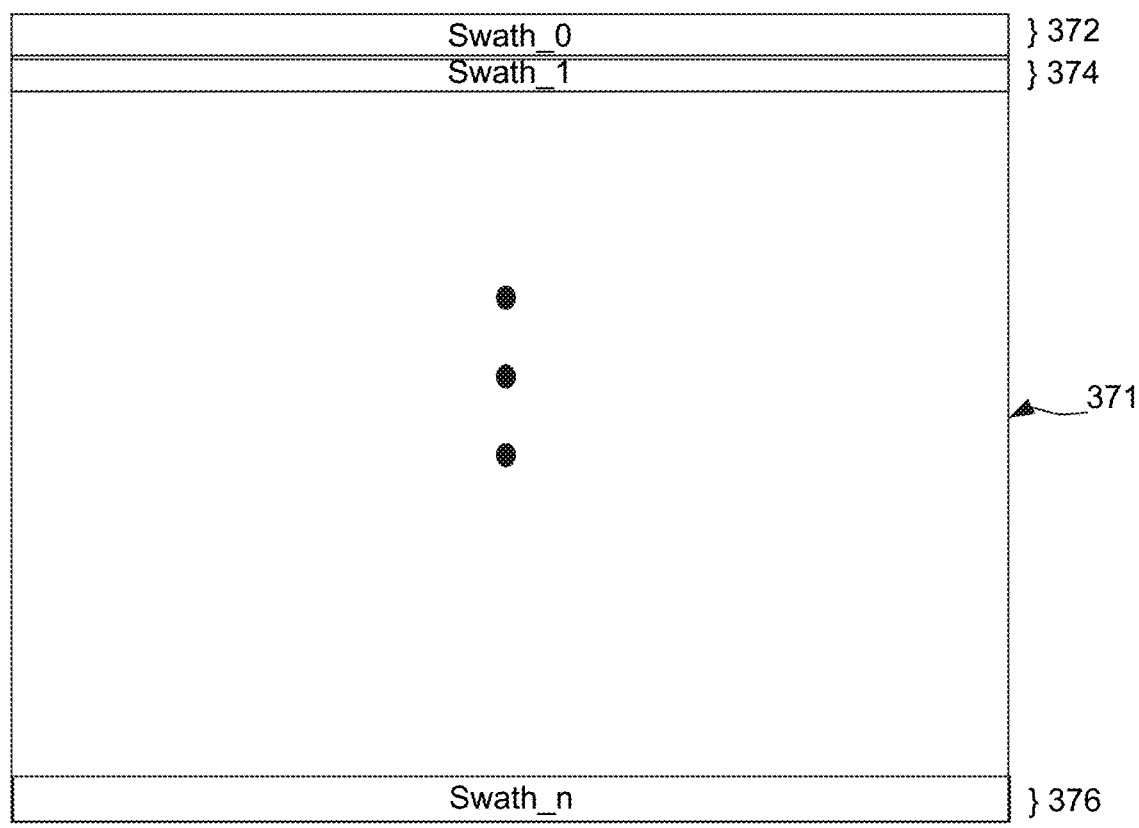
FIG. 3B shows a plurality of scanning swaths (Swath_1, Swath_2 . . . Swath_n) for the wafer of FIG. 3A.

FIG. 3A is a diagrammatic representation of a wafer scanning process for facilitating construction of a 3D intensity data structure in accordance with a specific implementation of the present invention. FIG. 3B shows a plurality of scanning swaths 371 (Swath_1, Swath_2 . . . Swath_n) for the wafer 350 of FIG. 3A. As shown in FIG. 3A, portion 354 is an enlargement of a portion 351 of wafer 350 having a row of dies (e.g., 356a~356e). In this illustrated example, a first focus is selected for scanning across two swaths of a row of the dies in a serpentine pattern. For instance, the inspection includes scanning an incident beam at a first focus setting and collecting image or intensity data in first direction (e.g., over swath_0), which moves from left to right, and scanning at the same first focus setting in an opposite second direction (e.g., over swath_1), which moves from right to left. Other scanning schemes can be employed. For example, the scanning can be achieved by moving either or both the stage and the incident beam so as to result in relative movement between the stage and beam. One example alternative scanning system is a retrace, flood system. In a flood system, the beam/illumination footprint is stationary, while the stage moves as the scanner. Also, the resolution of a flood illumination system is generally controlled by the imaging optics, instead of being controlled by the illumination spot size.

The next operation 208, for alignment of image sets of different focus setting, is only applicable after more than one set of image data has been collected for more than one focus setting. Thus, operation 208 is skipped for the first focus setting. Instead, it may then be determined whether there are more focus settings in operation 210 so as to cycle through each of a predefined set of focus settings. Thus, if there are more focus settings to select, the process continues to operation 204, in which a next focus setting is selected. Image data is collected for this next focus setting in operation 206.

The inspection may include continuously scanning across any number of the wafer's dies or die portions at a particular focus setting, and the scan pattern for each focus setting depends on any number factors. One factor is thermal expansion, which affects the actual focus setting or cross focus image alignment after the inspection tool has been operating for a particular period of time. For instance, it is beneficial to cycle through all the focus settings in a time that is less than the average or minimum time that it takes for thermal expansion to significantly affect the position settings, as well as how quickly the inspection tool can scan the swaths. The number of swaths can be scanned through focus in typically less than 5 minutes, by way of example. Cycling through the focus settings for 2 swaths seems to work well although other numbers may also work.

After two image data sets are collected for two focus settings, the image data sets that were collected at the different focus settings may also be aligned to build the 3D inspection data structure in operation 208. Alternatively, the image data may be aligned after all the image data sets are collected at the different focus settings.

Regardless of when the alignment process occurs, precise x/y spatial alignment between the through focus images is ideally achieved so as to fully utilize the 3D image data. In one embodiment, real-time x/y stage encoder data is collected to enable perfect alignment of images acquired at different focus height. The z stage encoder count is also recorded in real time so that the VM parameters can be extracted without error as further described below.

Figure 3C:
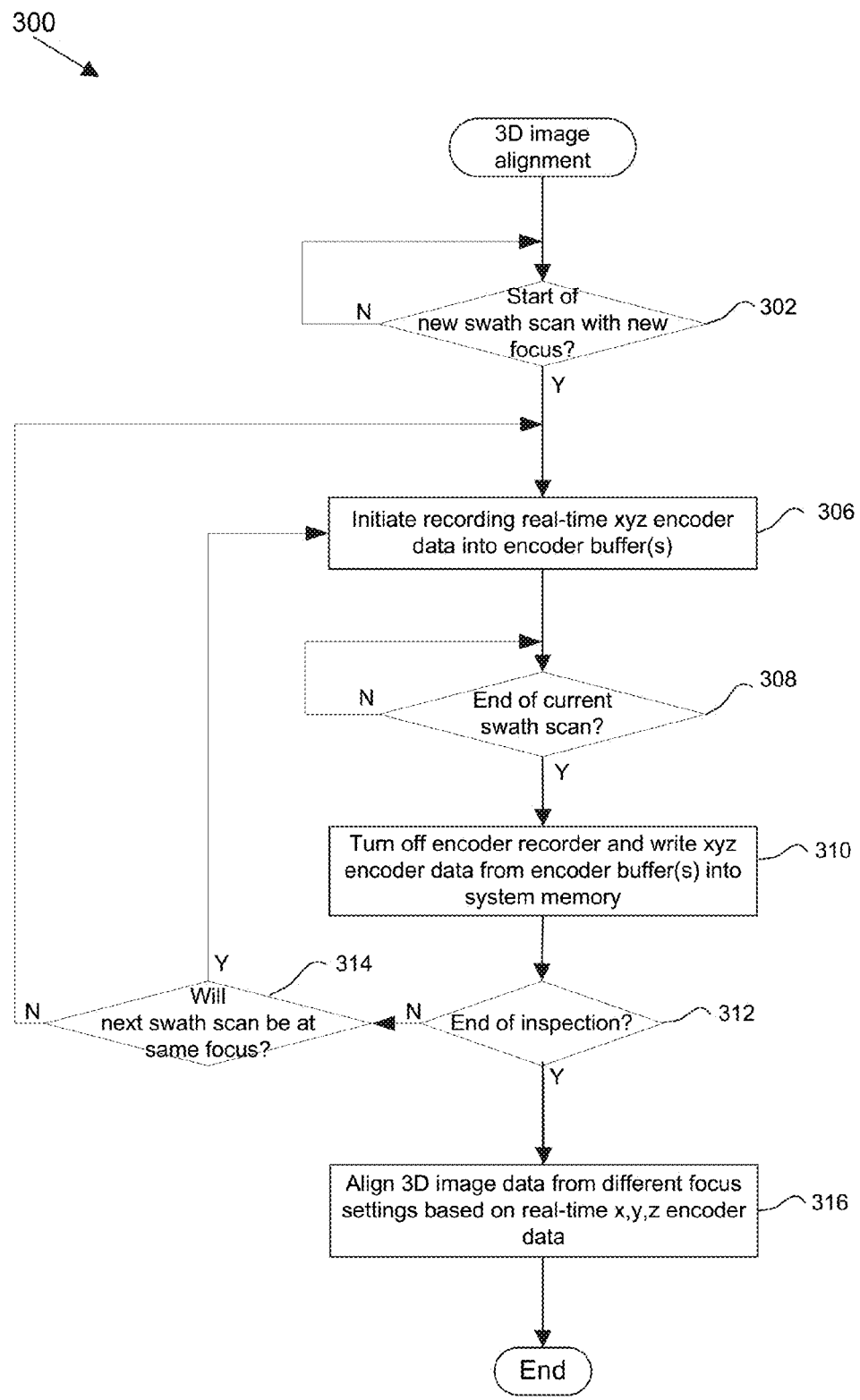
FIG. 3C is a flow chart illustrating an alignment procedure in accordance with one embodiment of the present invention.

Any suitable procedure may be utilized to align the 3D image data from different focus settings. FIG. 3C is a flow chart illustrating a 3D image alignment procedure 300 in accordance with one embodiment of the present invention. Initially, it may be determined whether a new swath scan has started with a new focus setting in operation 302. For example, the inspection tool is ready to scan swath 358a of FIG. 3A at a first focus setting.

To obtain encoder location data an instruction may be sent to the stage encoder system to record xyz position data into one or more encoder buffers, and then another instruction is sent to the stage encoder system to dump or "write" the xyz position data from the encoder buffers into the system memory.

While the xyz encoder system can be instructed to record real-time xyz encoder position data and write such data to the system memory as the swath is scanned, special firmware may be configured to enable real-time bi-directional communication. Alternatively, a sequential read/write technique would also work so that the system uses the scan turnaround time for writing and obtaining xyz encoder position data. An example encoder handling process is illustrated by FIG. 3C. Recording of real-time xyz encoder data into the encoder buffers may be initiated in operation 306. For instance, the encoder recorder is turned on at point 360a prior to the swath scan 358a (FIG. 3A). Thus, as image data is collected during swath scan 358a, the xyz encoder data is recorded into the encoder buffer.

It may then be determined whether the current swath scan has ended in operation 308. In the example of FIG. 3A, the process 300 waits for the swath scan 358a to finish. The encoder recorder can be turned off and the xyz encoder data can then be written from the encoder buffer(s) into the system memory in operation 310. For instance, the real-time encoder data sets are provided with its associated image data sets to an image processing system (e.g., system 700 of FIG. 7). As shown in FIG. 3A, the encoder recorder is turned off at point 360b after swath scan 358a, and then the encoder data sets can be dumped to the system at point 360c. This write process occurs while the stage is performing a swath turn-around process, which takes longer than the time for the xyz encoder data to be written into the system memory. Thus, the swath turn-around time can be performed in parallel to collecting the xyz encoder position data from the encoder buffer(s). For example, the stage is moving to a position to begin scanning the next swath 358b from right to left.

It may then be determined whether the inspection has ended in operation 312. For instance, it is determined whether the inspection tool has scanned all of the swaths. If inspection has not ended, it may then be determined whether the next swath scan will be performed at the same focus setting in operation 314. In the illustrated example, the next swath scan 358b is to be performed at the same focus setting as the previous swath scan 358a. Accordingly, the alignment process goes to operation 306, during which recording of real-time xyz encoder data is initiated. For example, the encoder recorder is turned on at point 360d of FIG. 3A. At the end of this swath scan 358b at the same focus setting, the encoder recorder is stopped again at point 360e, and the encoder data is dumped at point 360f. For a new focus setting, the process for obtaining encoder data is similar with the addition of also obtaining real-time z encoder data in operation 304. The alignment process is repeated until the current set of one or more swaths (e.g., 2 swaths) are scanned at all the focus settings. The 3D image data from the different focus settings can then be accurately aligned based on the real-time x,y,z encoder data in operation 316.

Referring back to FIG. 2, it may then be determined whether all the swaths have been scanned in operation 216. If more swaths remain, the process may then move to the next set of swaths in operation 218, and image collection is repeated for such swaths through focus as well as encoder position data collection.

In parallel to collecting encoder and image data from each set of one or more swaths at different focus settings, polynomial parameters may be extracted for each target and reference location from the aligned 3D image data in operation 212. Various analysis processes may then be performed on the extracted polynomial data to detect defects in the current set of one or more swaths in operation 214. That is, each set of 3D image data for specific swaths at through-focus can be analyzed as such 3D image data is constructed for each set of one or more swaths. An alternative less efficient example would entail analyzing the 3D image data after all swaths of the wafer are scanned through focus.

Figure 3D:
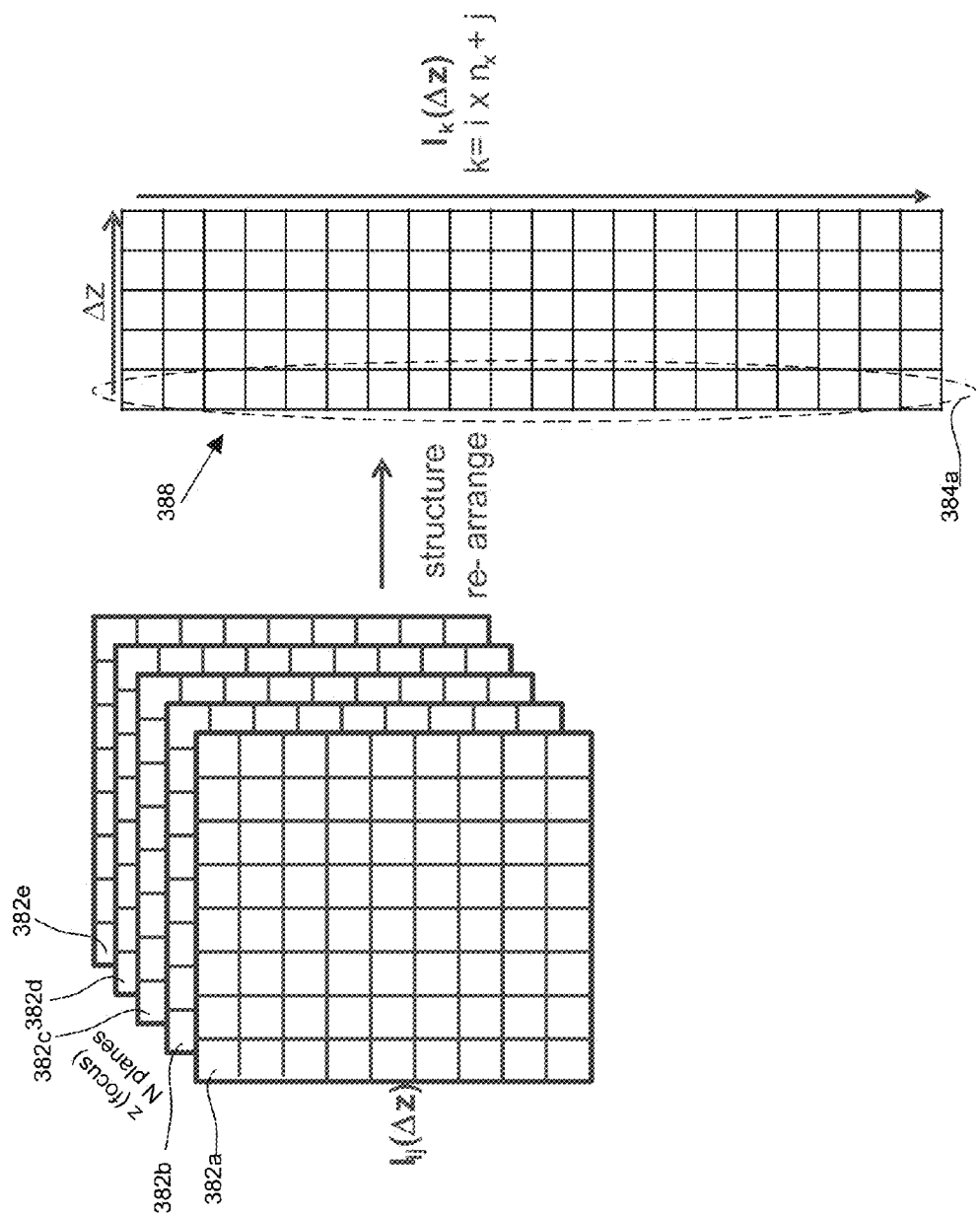
FIG. 3D is a diagrammatic representation of 3D image construction and volumetric (VM) parameter extraction in accordance with one embodiment of the present invention.

FIG. 3D is a diagrammatic representation of 3D image construction and VM parameter extraction in accordance with one embodiment of the present invention. This diagram illustrates formation of a polynomial expression having 5 terms with coefficients A~E.

The 3D image data, which is in the form of image planes 382a~382e, can first be rearranged into a 2D matrix 388. For instance, plane 382a is arranged into a first column, e.g., 384a, of 2D matrix 388. The other planes 382b~382e are each arranged into individual other ones of the columns of the 2D matrix 388. The following Equation [1] represents the collected intensity data in a 2D matrix:

$$I_{kl} = \sum_{m=0}^{4} T_{km} Z_{ml}$$

Equation [1]

The above Equation [1] represents a 2D matrix, $I_{kl}$, that is formed from m planes of image data at the different focus settings z, and has k rows (representing spatial imaging pixel intensity) and l columns (representing the different m planes). Each of the images is re-ordered such that a 2D image is represented as a vector. Each (i, j) in the original image is mapped into the k index such that k=i*nx+j. Note, i is the row index, and j is the column index. In other words, i represent position in y and j represent position in x. The matrix $T_{km}$ represents the coefficient values for different xy positions, which correspond to the different rows, and can be expressed by:

$$T = \begin{pmatrix} A_1 & B_1 & C_1 & D_1 & E_1 \\ A_2 & B_2 & C_2 & D_2 & E_2 \\ \ldots \\ A_k & B_k & C_k & D_k & E_k \end{pmatrix}$$

The matrix $Z_{ml}$ represents the changes in z for the different planes at which the 3D volumetric images are acquired, and can be expressed as:

$$Z = \begin{pmatrix} \Delta z_1^4 & \Delta z_2^4 & \ldots & \Delta z_{N_{plane-1}}^4 & \Delta z_{N_{plane}}^4 \\ \Delta z_1^3 & \Delta z_2^3 & \ldots & \Delta z_{N_{plane-1}}^3 & \Delta z_{N_{plane}}^3 \\ \Delta z_1^2 & \Delta z_2^2 & \ldots & \Delta z_{N_{plane-1}}^2 & \Delta z_{N_{plane}}^2 \\ \Delta z_1^1 & \Delta z_2^1 & \ldots & \Delta z_{N_{plane-1}}^1 & \Delta z_{N_{plane}}^1 \\ \Delta z_1^0 & \Delta z_2^0 & \ldots & \Delta z_{N_{plane-1}}^0 & \Delta z_{N_{plane}}^0 \end{pmatrix}$$

The coefficients matrix can then be determined by:

$$T_{km} = \sum_{m=1}^{N_{plane}} I_{kl} Z_{lm}^{-1}$$

The polynomial for the 3D image data can then be represented by:

$$I_{ij}(\Delta z) = A_{ij}\Delta z^4 + B_{ij}\Delta z^3 + C_{ij}\Delta z^2 + D_{ij}\Delta z + E_{ij}(\Delta z = 0)$$

The extracted volumetric (VM) coefficients can be used for any suitable purpose, for example, to increase defect/background contrast and/or extract higher than optical resolution spatial segmentation to enable definition of fine structures, such as definition of a SRAM micro care area.

In one application, the VM coefficients can be represented as VM images, containing the EM information from the wafer pattern and DOI, and these VM images can be used to enhance the visibility of DOI vs. background/nuisance. During detection, the VM images are obtained at both target and reference sites. In a three coefficient example, difference VIM images between the target and reference (denoted as $A_{dif}(x,y)$, $B_{dif}(x,y)$, and $C_{dif}(x,y)$) can be determined.

Figure 4:
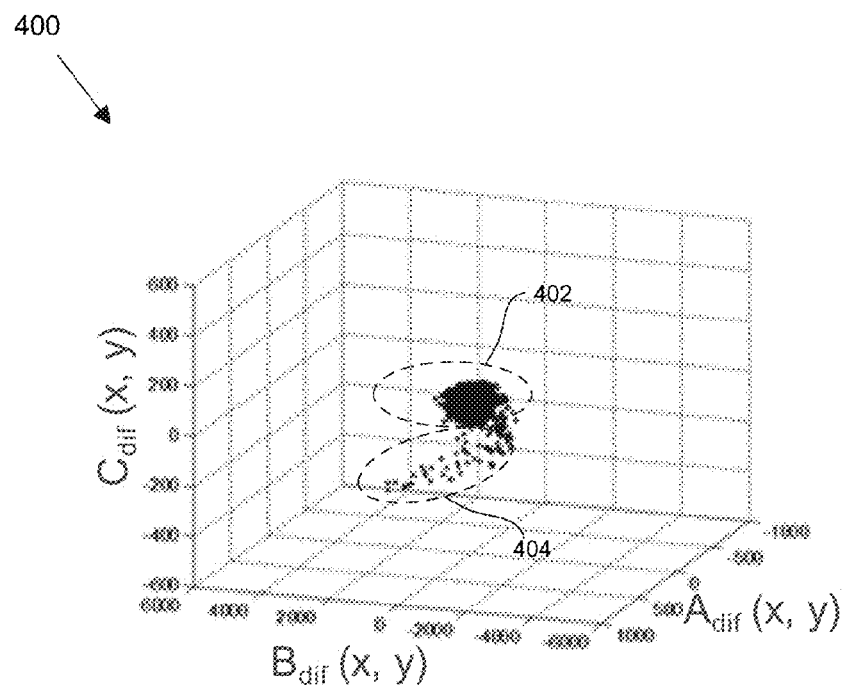
FIG. 4 is a 3D scatter plot that was constructed from example difference VM images in accordance with one embodiment of the present invention.

In theory, a DOI has either a different physical appearance (such as physical defects) from the background and/or is composed of different material from the background (such as contaminants). Therefore, the EM response from the DOI is expected to be different from the EM response of the background. Accordingly, examining differences in VM parameters should lead to better differentiation of DOI vs nuisance/background. This theory was tested on patterned wafers. FIG. 4 is a 3D scatter plot that was constructed from example difference VM images in accordance with one embodiment of the present invention. From this example 3D scatter plot, which are constructed by $A_{dif}(x,y)$, $B_{dif}(x,y)$, and $C_{dif}(x, y)$, it is clear that the DOI pixels 404 are substantially different from the background pixels 402. Clustering processes may be implemented to distinguish DOI pixels from nuisance/background pixels. Any suitable clustering process may be used. Examples include nearest neighbor clustering, centroid clustering, distribution-based clustering, density based clustering, etc.

To make the distinction between DOI and background/nuisance easier, each point in the 3D scatter plot can be projected into a unit sphere. The projection allows each point to have designated angular position, (Θ, φ). Pixels outside of ($\Theta_{DOI}$, $\phi_{DOI}$) within set range of angular tolerance ranges can be filtered out to enhance the DOI/nuisance visibility. That is, outliers in the 3D projection (or scatter plot) can be designated as DOI's. An angular filter may be applied to the projected points so that visibility of defects is substantially enhanced.

The difference pixels can be thresholded for defect detection. For instance, if a filtered difference value (absolute value) between the reference and target is larger than a predefined threshold, the pixel can be defined as a defect of interest (DOI), and reviewed as a defect candidate. The scatter plot or projected pixels can be thresholded. Additionally, certain regions (or clusters of points) of the scatter plot or angular (clustered) regions of the 3D projection can be assigned different thresholds. For instance, outlier regions can be assigned a more sensitive threshold so that defects are found more often, while non-outlier or clustered regions can be assigned a less sensitive threshold or not thresholded.

Figure 5B:
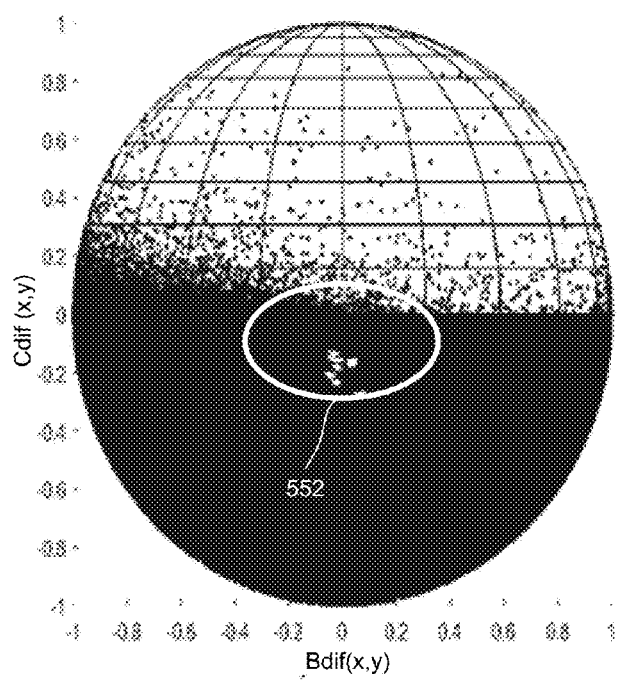
FIG. 5B shows an example of a projected unit sphere with DOI pixels and background/nuisance pixels separation in accordance with one embodiment of the present invention.
Figure 5A:
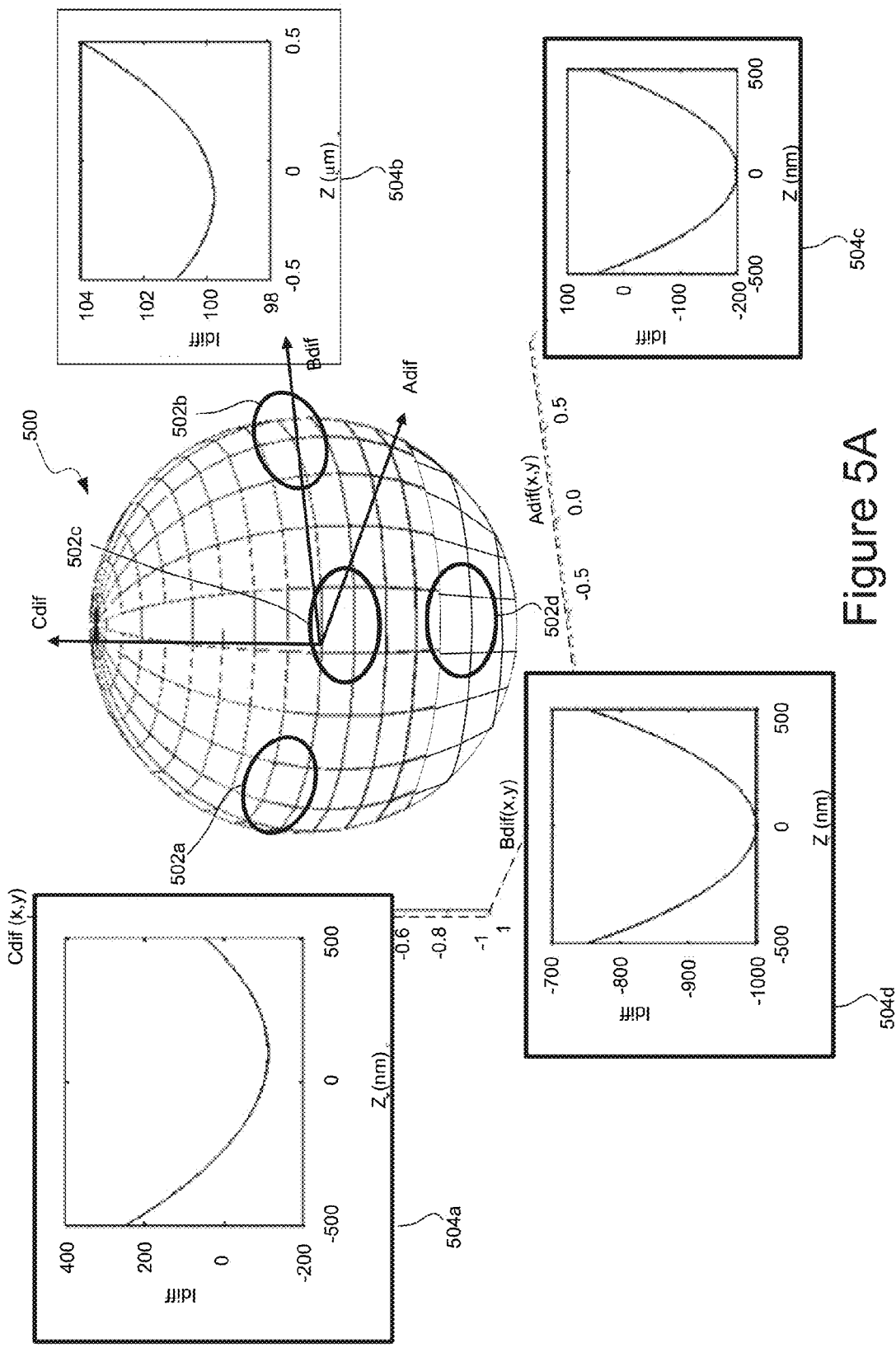
FIG. 5A illustrates a 3D projection of VM difference image pixels onto a unit sphere in accordance with one embodiment of the present invention.

FIG. 5A illustrates a 3D projection of VM difference image pixels onto a unit sphere 500 in accordance with one embodiment of the present invention. FIG. 5B shows an example of a projected unit sphere with DOI pixels 552 and background/nuisance pixels (not labelled). The unit sphere 500 (FIG. 5A) has three dimensions: Cdif, $B_{dif}$ and $C_{dif}$.

Based on experimental data, different regions of a sphere onto which pixel values are projected tend to contain DOI's. For example, regions 502a, which corresponds to plot 504a, tends to include DOI's that have optimal focus locations that are away from zero focus plane and have DOI's with a relatively weak signal strength. Likewise, region 502b (corresponding to plot 504b) has relatively weak signal strength DOI's at non-zero optimal focus. Conversely, region 502c (corresponding to plot 504c) and region 502d (corresponding to plot 504d) tend to have DOI's at an optimal focus of zero. However, only region 504d tends to have DOI's with a relatively strong signal strength, while regions 504c has DOI's with a relatively weak signal strength. As a result, the DOI's from certain clustered regions can be selected for further analysis (e.g., thresholding) or be analyzed with more sensitivity (e.g., more sensitive threshold) than other regions. The location of a strong/weak object that is projected onto the sphere can be understood by looking at the behavior of the polynomial function. The $C_{dif}$(x, y) is the constant term in the polynomial function. This constant term describes the magnitude of global maximum (downward $2^{nd}$ order polynomial) or global minimum (upward $2^{nd}$ order polynomial). Larger $C_{dif}$ corresponds to larger magnitude of global maximum or global min; hence, stronger defect. The sphere with large $C_{dif}$ is plotted on the upper or lower hemisphere (e.g., 502d of FIG. 5A).

In another application of using the 3D image data, focus fusion can be implemented. If the nature of DOI and background/nuisance are different, it is expected that the through focus behavior of DOI and nuisance/background can be different. Focus fusion is a technique to further differentiate DOI and nuisance. Focus fusion can be implemented by combining the intensity across the focus planes values together for each pixel in any suitable manner. In one implementation, the intensity across the focus planes are multiplied together to form a composite image that more clearly shows DOI's. For instance, a fusion image is formed by multiplying Image(x, y, deltaZ_1)*Image(x, y, deltaZ_2), etc. A composite image formed by this focus fusion method will tend to have a relatively higher signal-to-noise ratio (SNR) than the original fixed focus plane images. Focus fusion can be combined with the VM angular projection and angular filter technique to obtain a filtered composite image having a higher SNR than the composite and original images. The resulting composite images of target and reference areas can then be thresholded as described above.

Figure 6:
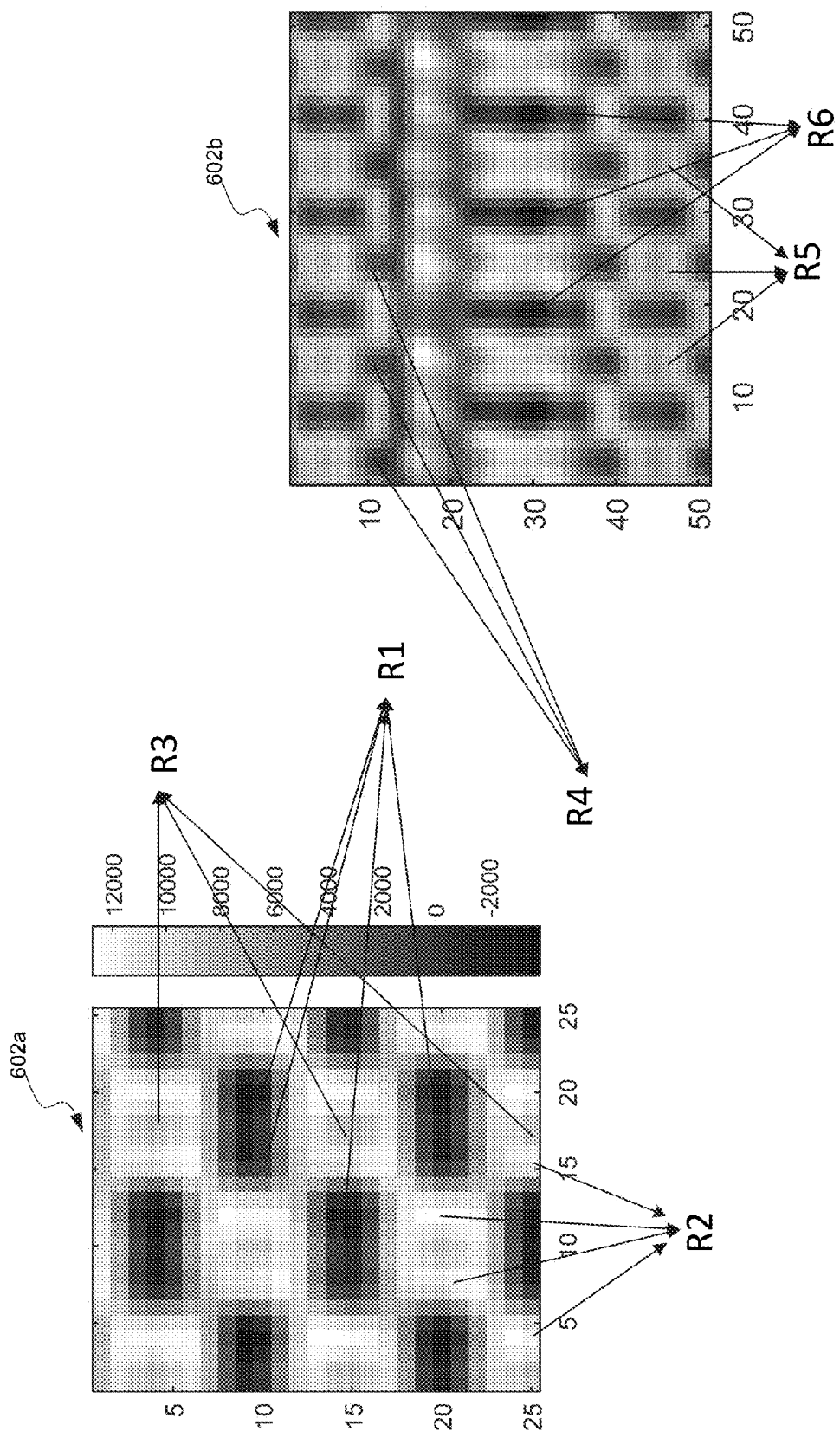
FIG. 6 shows an example of region segmentation based on extracted VM parameters in accordance with another embodiment of the present invention.

The extracted VM parameters can also be used to extract device structure that is not resolvable by optical resolution. As mentioned above, VM parameters are closely link to the electromagnetic field generated from the wafer pattern. The information can be used to dissect the optical images into different micro regions based on the EM field emitted from the wafer. FIG. 6 shows an example of region segmentation based on extracted VM parameters in accordance with another embodiment of the present invention. Two magnified image portions 602a and 602b of a dissected image are shown. The entire optical image is not shown for clarity purposes. Based on VM parameter properties, each image can be segmented into different regions, and each region can be represented by a different color (shown as black and white outlined areas in FIG. 6) or other identifier so as to distinguish the different regions form each other. For instance, image portion 602a contains regions R1, R2, and R3, while image portion 602b contains regions R4, R5, and R6. The different regions can be seen to correspond to actual device structures. The different segments can be analyzed with different levels of care. For instance, segments that correspond to particular sensitive SRAM structure can be analyzed at more sensitive thresholds than other structures.

In an alternative embodiment, the intensity change that is collected through focus ($\Delta I/\Delta z$) can be used to compare differences between reference and target images. By taking $\Delta I/\Delta Z$ measurement, intensity measurement may become phase sensitive so as to provide higher sensitivity, especially for phase change induced by defects. For example, newly generated difference images between reference and target images, which are calculated on intensity derivative over defocus, can be used to detect defects via adaptive thresholding techniques.

In one example, the difference of intensity for two different focus setting at the same x-y location may first be determined. This difference calculation may be performed on an area, not just at single point, how (dI)/(dz) is changing in x and y is of interest. If there are images from more than 2 focus, one approach more accurately estimates (dI)/(dz) by (I1−I2)/(delta z), where higher order terms are neglected. As (dI)/(dz) should be mathematically a smooth function, having multiple measurements from multiple focal planes can provide a better estimate on (dI)/(dz).

For example, a set of image weights are selected such that all but the 1st order. In another approach, a simple curve fitting technique will offer better performance, at the cost of more computation time. In this technique, the intensity vs. z data for each pixel is fit to a polynomial model, and then the desired first order component is extracted for computing phase. By fitting to higher order polynomials, a more accurate estimate of the first order derivative can be obtained. A least-squares fit to polynomials, which weights all images equally, may be used. The order of the polynomial fit function is generally less than the number of images used, and more images will result in better noise performance, without sacrificing accuracy. Computationally, each pixel may be treated independently, and fit to a polynomial by standard fitting techniques (least-squares curve fit). The pixel-wise treatment lends itself well to parallel computing, such as computation on a Graphics Processing Unit (GPU).

Figure 7:
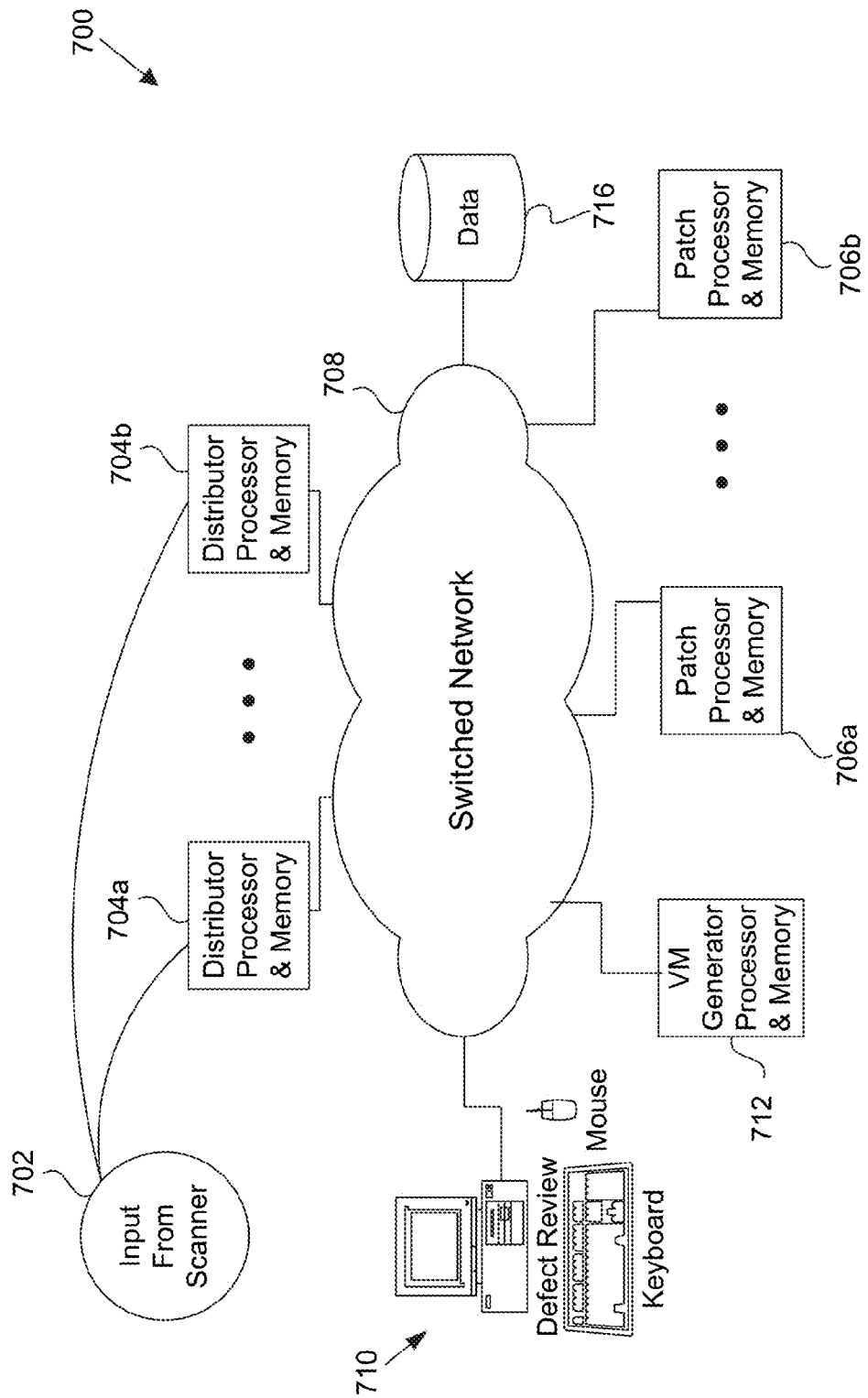
FIG. 7 is a diagrammatic representation of an example inspection system in which techniques of the present invention may be implemented FIG. 8 provides a schematic representation of an inspection apparatus in accordance with certain embodiments.

Techniques of the present invention may be implemented in any suitable combination of hardware and/or software. FIG. 7 is a diagrammatic representation of an example inspection system 700 in which techniques of the present invention may be implemented. The inspection system 700 may receive input 702 from an inspection tool or scanner (not shown). The inspection system may also include a data distribution system (e.g., 704a and 704b) for distributing the received input 702, an intensity signal (or patch) processing system (e.g., patch processors and memory 706a and 706b) for processing specific portions/patches of received input 702, a VM generator system (e.g., VM Generator Processor and Memory 712) for generating 3D image data at multiple focus, etc., a network (e.g., switched network 708) for allowing communication between the inspection system components, an optional mass storage device 716, and one or more inspection control and/or review stations (e.g., 710) for reviewing the inspection results. Each processor of the inspection system 700 typically may include one or more microprocessor integrated circuits and may also contain interface and/or memory integrated circuits and may additionally be coupled to one or more shared and/or global memory devices.

The scanner or data acquisition system (not shown) for generating input data 702 may take the form of any suitable instrument (e.g., as described further herein) for obtaining intensity signals or images of a wafer. For example, the scanner may construct an optical image or generate intensity values of a portion of the wafer based on a portion of detected light that is reflected, transmitted, or otherwise directed to one or more light sensors. The scanner may then output the intensity values or images, as well as encoder position data, to the inspection system.

The wafer is generally divided into a plurality of patch portions from which multiple intensity values from multiple points are obtained. The patch portions of the wafer can be scanned to obtain this intensity data. The patch portions may be any size and shape, depending on the particular system and application requirements. In general, multiple intensity values for each patch portion may be obtained by scanning the wafer in any suitable manner. By way of example, multiple intensity values for each patch portion may be obtained by raster scanning the wafer. Alternatively, the images may be obtained by scanning the wafer with any suitable pattern, such as a circular or spiral pattern. Of course, the sensors may have to be arranged differently (e.g., in a circular pattern) and/or the wafer may be moved differently (e.g., rotated) during scanning in order to scan a circular or spiral shape from the wafer.

In the example illustrated below, as the wafer moves past the sensors, light is detected from a rectangular region (herein referred to as a "swath") of the wafer and such detected light is converted into multiple intensity values at multiple points in each patch. In this embodiment, the sensors of the scanner are arranged in a rectangular pattern to receive light that is reflected and/or transmitted from the wafer and generate therefrom a set of intensity data that corresponds to a swath of patches of the wafer. In a specific example, each swath can be about 1 million pixels wide and about 1000 to 2000 pixels high, while each patch can be about 2000 pixels wide and 1000 pixels high.

Intensity values for each patch may be obtained using an optical inspection tool that is set up in any suitable manner. The optical tool is generally set up with a set of operating parameters or a "recipe" that is substantially the same for the different inspection runs for obtaining intensity values. Recipe settings may include one or more of the following settings: a setting for scanning the wafer in a particular pattern, pixel size, a setting for grouping adjacent signals from single signals, focus settings, an illumination or detection aperture setting, an incident beam angle and wavelength setting, a detector setting, a setting for the amount of reflected or transmitted light, aerial modeling parameters, etc.

Intensity or image data, including encoder position data, 702 can be received by data distribution system via network 708. The data distribution system may be associated with one or more memory devices, such as RAM buffers, for holding at least a portion of the received data 702. Preferably, the total memory is large enough to hold an entire swath of data. For example, one gigabyte of memory works well for a swath that is 1 million by 1000 pixels or points.

The data distribution system (e.g., 704a and 704b) may also control distribution of portions of the received input data 702 to the processors (e.g. 706a and 706b). For example, data distribution system may route data for a first patch (at multiple focus settings) to a first patch processor 706a, and may route data for a second patch (at multiple focus settings) to patch processor 706b. Multiple sets of data for multiple patches may also be routed to each patch processor.

The patch processors may receive intensity values or an image that corresponds to at least a portion or patch of the wafer. The patch processors may each also be coupled to or integrated with one or more memory devices (not shown), such as DRAM devices that provide local memory functions, such as holding the received data portion. Preferably, the memory is large enough to hold data that corresponds to a patch of the wafer. For example, a patch may be 512 by 1024 pixels. The patch processors may also share memory.

Each set of input data 702 may correspond to a swath of the wafer. One or more sets of data may be stored in memory of the data distribution system. This memory may be controlled by one or more processors within the data distribution system, and the memory may be divided into a plurality of partitions. For example, the data distribution system may receive a data set corresponding to a portion of a swath into a first memory partition (not shown), and the data distribution system may receive another data set corresponding to another swath into a second memory partition (not shown). Preferably, each of the memory partitions of the data distribution system only holds the portions of the data that are to be routed to a processor associated with such memory partition. For example, the first memory partition of the data distribution system may hold and route first data to patch processor 706a, and the second memory partition may hold and route second data to patch processor 706b.

The incident light or detected light may be passed through any suitable spatial aperture to produce any incident or detected light profile at any suitable incident angles. By way of examples, programmable illumination or detection apertures may be utilized to produce a particular beam profile, such as dipole, quadrapole, quasar, annulus, etc. In a specific example, Source Mask Optimization (SMO) or any pixelated illumination technique may be implemented. In other embodiments, a polarizer and analyzer are used to obtained polarized intensity/image data.

The data distribution system may define and distribute each set of data of the data based on any suitable parameters of the data. For example, the data may be defined and distributed based on the corresponding position of the patch on the wafer. In one embodiment, each swath is associated with a range of column positions that correspond to horizontal positions of pixels within the swath. For example, columns 0 through 256 of the swath may correspond to a first patch, and the pixels within these columns will comprise the first image or set of intensity values, which is routed to one or more patch processors. Likewise, columns 257 through 512 of the swath may correspond to a second patch, and the pixels in these columns will comprise the second image or set of intensity values, which is routed to different patch processor(s). The columns may be aligned by the system based on the encoder position data, or aligned by the scanner.

Figure 8:
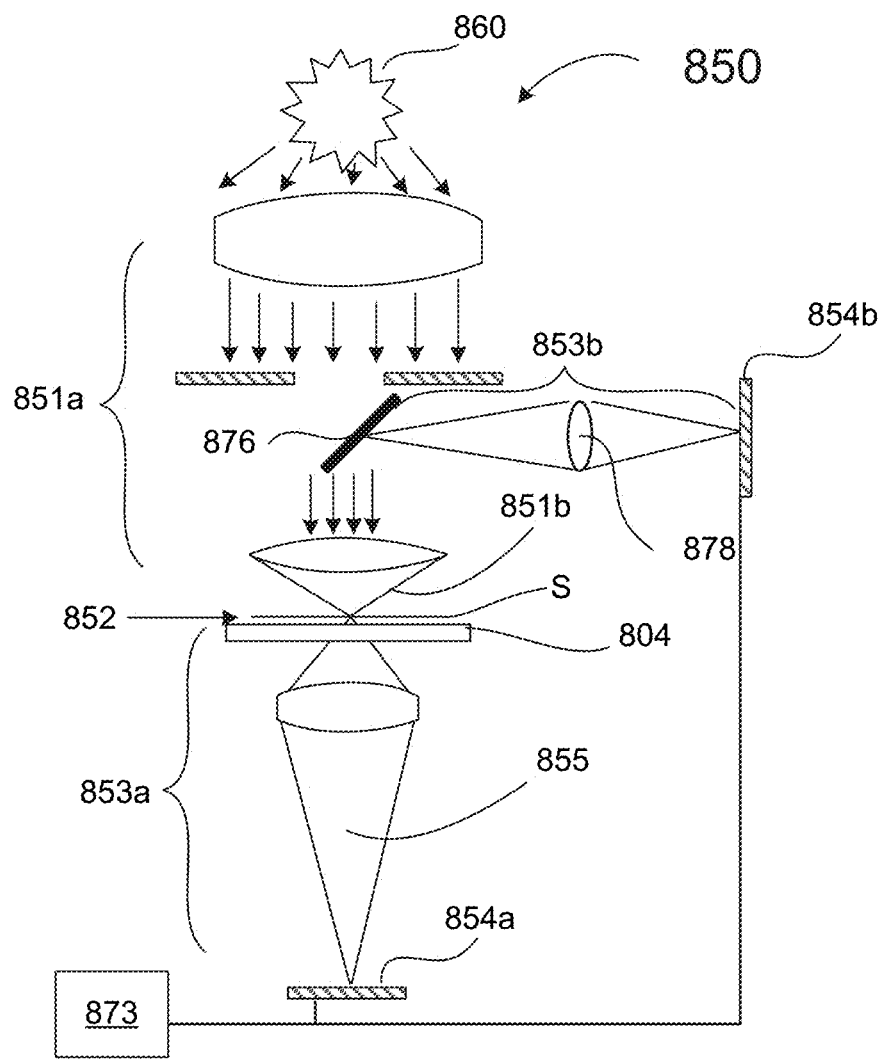

The inspection scanning techniques described herein may be implemented on or with respect to images and encoder position data obtained from various specially configured inspection systems, such as the one schematically illustrated in FIG. 8. The illustrated system 850 includes an illumination source 860 producing at least one light beam that is directed through illumination optics 851a onto a sample S, such as a photomask or wafer, in plane 852. The inspection system 850 may have a numerical aperture 851b at plane 852. The illumination optics 851a may also include various lens and modules for achieving one or more incident beams with different characteristics. The sample S to be inspected/measured is placed on a stage mechanism 804 at the plane 852 and exposed to the source. The stage mechanism will include an encoder that is operable to record encoder position information in its encoder buffer and write such data to be received by the system of FIG. 7, by way of example.

The transmitted image from a sample S (e.g., a mask) can be directed through a collection of optical elements 853a, which project the patterned image onto a sensor 854a. Optical elements (e.g., beam splitter 876 and detection lens 878) are arranged to direct and capture the reflected and/or scattered light from the sample S onto sensor 854b. Suitable sensors include charged coupled devices (CCD), CCD arrays, time delay integration (TDI) sensors, TDI sensor arrays, photomultiplier tubes (PMT), and other sensors. Certain inspection tools may include only the reflecting collection optics 853b (or other scattering optics) and sensor 854b, excluding optics 853a and sensor 854a.

The illumination optics column may be moved respect to the mask stage and/or the stage moved relative to a detector or camera by any suitable mechanism so as to scan patches of the reticle. For example, a motor mechanism may be utilized to move the stage. The motor mechanism may be formed from a screw drive and stepper motor, linear drive with feedback position, or band actuator and stepper motor, by way of examples.

The through focus image acquisition can be achieved by either moving the stage (804) up and down or by moving the detectors (854b) along the optical axis or moving both the stage and the detectors.

The signals captured by each sensor (e.g., 854a and/or 854b) can be processed by a controller system 873, such as by one or more signal processing devices, which may each include an analog-to-digital converter configured to convert analog signals from each sensor into digital signals for processing. The controller system 873 may include one or more processors coupled to input/output ports, and one or more memories via appropriate buses or other communication mechanisms.

The controller system 873 may also include one or more input devices (e.g., a keyboard, mouse, joystick) for providing user input, such as changing focus and other inspection recipe parameters. The controller system 873 may also be connected to the stage positioning mechanism for controlling, for example, a sample position (e.g., focusing and scanning) and connected to other inspection/metrology system components for controlling other inspection parameters and configurations of such components.

The controller system 873 may be configured (e.g., with programming instructions) to provide a user interface (e.g., a computer screen) for displaying resultant intensity values, images, and other inspection/metrology results. The controller system 873 may be configured to generate 3D image structures, extracted coefficients, fusion results, segmentation images, projected data, and/or other transformations of reflected and/or transmitted sensed light beam. The controller system 873 may be configured (e.g., with programming instructions) to provide a user interface (e.g., on a computer screen) for displaying resultant intensity values, images, plots, projections, and other inspection/metrology characteristics. In certain embodiments, the controller system 873 is configured to carry out inspection techniques detailed above.

Because such information and program instructions may be implemented on a specially configured computer system, such a system includes program instructions/computer code for performing various operations described herein that can be stored on a non-transitory computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a semiconductor wafer includes at least one memory and at least one processor that are configured to perform techniques described herein. Examples of an inspection system include specially configured 29xx, 8xxx, or 3xxx inspection system families available from KLA-Tencor of Milpitas, Calif.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the inspection intensity data may be obtained from a transmitted, reflected, or a combination output beam. Accordingly, the present embodiments are to be considered as illustrative and not restrictive, and the invention is not to be limited to the details given herein.

What is claimed is:

1. A method for detecting defects on a semiconductor sample, the method comprising:
using an inspection tool to collect intensity data sets at a plurality of focus settings from each of a plurality of xy positions of the sample;
extracting a polynomial equation having a plurality of coefficients for each of the xy position's collected intensity data sets as a function of focus setting;
representing each of the coefficients' set of values for the plurality of xy positions with a corresponding coefficient image plane to form a plurality of coefficient image planes; and
analyzing a plurality of difference coefficient image planes that are based on comparison of a target set of the coefficient image planes and a reference set of the coefficient image planes to detect defects on the sample.

2. The method of claim 1, wherein intensity data is collected at the plurality of focus settings from a first set of one or more swaths before a next set of one or more swaths, wherein a number of the swaths in the first and next swaths, from which the intensity data is collected, is selected to be less than a thermal expansion time for affecting an actual focus position.

3. The method of claim 2, wherein the number of swaths comprises a first and second swath.

4. The method of claim 3, further comprising:
collecting real-time xy and z encoder position data from the inspection tool; and
prior to extracting the polynomial equation for each of the xy positions' collected intensity data sets, aligning the collected intensity data from each focus setting based on the collected real-time xy position data.

5. The method of claim 4, wherein intensity data is collected from the first and second swath of xy positions at the plurality of focus settings before the aligning operation is performed.

6. The method of claim 2, further comprising
initiating recording of xy encoder position data into an encoder buffer prior to collect intensity data from a first one of the swaths at a first one of the focus settings,
while the inspection tool's stage is turning around to setup for collecting intensity data from a second one of the swaths at the first focus setting, copying the xy encoder position data from the encoder buffer into a system memory for accessing for use in the aligning operation and then initiating recording of xy encoder position data into the encoder buffer prior to collecting intensity data from the second swath;
while the inspection tool's stage is turning around to setup for collecting intensity data from the first swath at a second one of the focus settings after collecting intensity data from the second swath, copying the xy encoder position data from the encoder buffer into a system memory for accessing for use in the aligning operation and then initiating recording of xy encoder position data into the encoder buffer prior to collected intensity data from the first swath at the second focus setting; and
repeating the operations of initiating recording and copying for subsequent pairs of swaths at each of the focus settings.

7. The method of claim 1, wherein analyzing is performed by:
calculating the plurality of difference coefficient image planes having a plurality of difference coefficient values for each coefficient by subtracting each of the target set from each of the reference set.

8. The method of claim 7, wherein the difference coefficient image planes are analyzed by plotting an image point for the difference coefficient values at each xy position from the difference coefficient image planes into a scatter plot having an axis for each coefficient and clustering such scatter plot's image points into clusters of defects of interest image points, nuisance image points, or background image points.

9. The method of claim 7, wherein the difference coefficient image planes are analyzed by projecting an image point for the difference coefficient values for each xy position from the difference coefficient image planes onto a unit sphere and clustering such projected image points into clusters of defects of interest image points, nuisance image points, or background image points.

10. The method of claim 7, wherein the difference coefficient image planes are analyzed by:
   generating a plurality of difference images from intensity data sets collected from a target and a reference at each focus plane;
   combining the difference images to form a fused image across focus; and
   analyzing the fused image for defect detection.

11. The method of claim 7, further comprising:
   grouping the coefficients with similar values together so as to form a plurality of different segments, wherein each segment corresponds to different portion of an actual device structure;
   analyzing the different segments with different stringency for detecting defects based on which type of actual devices correspond to the different segments.

12. The method of claim 1, further comprising analyzing a difference between intensity changes as a function of focus setting changes for each xy position in a second target set of intensity data sets and a second reference set of intensity data sets.

13. The method of claim 1, wherein the focus settings are comprised of pairs of focus setting, wherein each pair of focus setting is separated by a step value that is within a fraction of the depth of focus of the inspection system.

14. An inspection system for inspecting a semiconductor sample, comprising:
   an illumination source for generating an incident beam;
   illumination optics for directing the incident beam towards a semiconductor sample at a plurality of focus settings;
   a sensor for collecting intensity data sets at a plurality of focus settings from each of a plurality of xy positions of the sample in response to the incident beam; and
   a controller that is configured to perform the following operations:
      extracting a polynomial equation having a plurality of coefficients for each of the xy position's collected intensity data sets as a function of focus setting;
      representing each of the coefficients' set of values for the plurality of xy positions with a corresponding coefficient image plane to form a plurality of coefficient image planes; and
      analyzing a plurality of difference coefficient image planes that are based on comparison of a target set of the coefficient image planes and a reference set of the coefficient image planes to detect defects on the sample.

15. The inspection system of claim 14, wherein intensity data is collected at the plurality of focus settings from a first set of one or more swaths before a next set of one or more swaths, wherein a number of the swaths in the first and next swaths, from which the intensity data is collected, is selected to be less than a thermal expansion time for affecting an actual focus position.

16. The inspection system of claim 15, wherein the number of swaths comprises a first and second swath.

17. The inspection system of claim 16, wherein the controller is further configured for:
   collecting real-time xy and z encoder position data from the inspection tool; and
   prior to extracting the polynomial equation for each of the xy positions' collected intensity data sets, aligning the collected intensity data from each focus setting based on the collected real-time xy position data.

18. The inspection system of claim 15, further comprising:
   a stage for receiving the sample;
   an encoder buffer for storing encoder position data for the sample; and
   a system memory,
   wherein the controller is further configured for:
   initiating recording of xy encoder position data into the encoder buffer prior to collect intensity data from a first one of the swaths at a first one of the focus settings,
   while the inspection system's stage is turning around to setup for collecting intensity data from a second one of the swaths at the first focus setting, copying the xy encoder position data from the encoder buffer into the system memory for accessing for use in the aligning operation and then initiating recording of xy encoder position data into the encoder buffer prior to collecting intensity data from the second swath;
   while the inspection t system's stage is turning around to setup for collecting intensity data from the first swath at a second one of the focus settings after collecting intensity data from the second swath, copying the xy encoder position data from the encoder buffer into the system memory for accessing for use in the aligning operation and then initiating recording of xy encoder position data into the encoder buffer prior to collected intensity data from the first swath at the second focus setting; and
   repeating the operations of initiating recording and copying for subsequent pairs of swaths at each of the focus settings.

19. The inspection system of claim 14, wherein analyzing is performed by:
   calculating the plurality of difference coefficient image planes having a plurality of difference coefficient values for each coefficient by subtracting each of the target set from each of the reference set.

20. The inspection system of claim 19, wherein the analyzing the difference coefficient image planes is accomplished by:
   generating a plurality of difference images from intensity data sets collected at each focus Plane;
   combining the difference images to form a fused image across focus; and
   analyzing the fused image for defect detection.

21. The inspection system of claim 19, wherein the difference coefficient image planes are analyzed by plotting an image point for the difference coefficient values at each xy position from the difference coefficient image planes into a scatter plot having an axis for each coefficient and clustering such scatter plot's image points into clusters of defects of interest image points, nuisance image points, or background image points.

22. The inspection system of claim 19, wherein the difference coefficient image planes are analyzed by projecting an image point for the difference coefficient values for each xy position from the difference coefficient image planes onto a unit sphere and clustering such projected image points into clusters of defects of interest image points, nuisance image points, or background image points.

23. The inspection system of claim 19, wherein the difference coefficient image planes are analyzed by combining the difference coefficient images planes into a single fusion image and analyzing the fusion image for defect detection.

24. The inspection system of claim 19, wherein the controller is further configured for:
grouping the coefficients with similar values together so as to form a plurality of different segments, wherein each segment corresponds to different portion of an actual device structure;
analyzing the different segments with different stringency for detecting defects based on which type of actual devices correspond to the different segments.

25. The inspection system of claim 14, wherein the controller is further configured for:
analyzing a difference between intensity changes as a function of focus setting changes for each xy position in a second target set of intensity data sets and a second reference set of intensity data sets.

* * * * *